United States Patent [19]

Abbey

[11] Patent Number: 5,057,094

[45] Date of Patent: Oct. 15, 1991

[54] CONVENIENT EMPTYING OR URINARY LEG BAG

[76] Inventor: Sylvia Abbey, 5131 West Oakland Park Blvd., Ft. Lauderdale, Fla. 33313

[21] Appl. No.: 554,463

[22] Filed: Jul. 19, 1990

Related U.S. Application Data

[63] Continuation-in-part of Ser. No. 332,979, Apr. 4, 1989, abandoned.

[51] Int. Cl.$^5$ ............................................. A61F 5/44
[52] U.S. Cl. .................................... 604/351; 604/327
[58] Field of Search ............... 604/327, 343, 344, 345, 604/351, 352, 353; 2/DIG. 7

[56] References Cited

U.S. PATENT DOCUMENTS

| 3,357,430 | 12/1967 | Rosenberg | 604/353 |
| 4,073,295 | 2/1978 | Laufbahn | 604/353 |
| 4,713,067 | 12/1987 | Rothenberg et al. | 604/351 |

FOREIGN PATENT DOCUMENTS 0148731  7/1985  European Pat. Off. .......... 2/DIG. 7

Primary Examiner—Randy Citrin Shay
Attorney, Agent, or Firm—Richard C. Litman

[57] ABSTRACT

A method and device for draining urine from a urinary leg bag without inconvenience to the wearer. The bag is attached to the leg of the wearer with straps above and below the protrusion of the calf. Trousers that cover the bag have a flexible intermeshing closure at the bottom on one trouser leg to allow access to the urinary leg bag for draining into a receptacle.

6 Claims, 1 Drawing Sheet

CONVENIENT EMPTYING OR URINARY LEG BAG

CROSS-REFERENCE TO RELATED APPLICATION

This application is a continuation-in-part of application Ser. No. 07/332,979 filed Apr. 4, 1989, now abandoned.

Application Ser. No. 07/074,237 filed July 2, 1987 by Sylvia Abbey, now abandoned, contains related material.

BACKGROUND OF THE INVENTION

1. Field of the Invention

This invention relates to the use of disposable urinary leg bags. In particular, it relates to a garment which makes the emptying of such bags more convenient.

In the treatment of certain diseases that lead to urinary incontinence, it is necessary to employ a catheter which is inserted into the urinary tract so as to collect the urine in a urinary bag. Urinary bags can be worn on the leg by means of straps and thus provide mobility for the patient.

2. Description of the Prior Art

U.S. Pat. No. 501,372 to Sherman discloses a urinary bag that is worn on the leg.

U.S. Pat. No. 3,115,641 to Rea discloses trousers with a flexible intermeshing closure.

These patents, or other apparatus used to empty urinary leg bags, either singly or in combination do not disclose the novel method and apparatus described and claimed herein.

SUMMARY OF THE INVENTION

The periodic emptying of a urinary bag, which is necessitated by the accumulation of urine, is awkward, inconvenient and embarrassing to the wearer of the bag, the user having to remove clothing in order to have access to the urinary bag. This is particularly true for men with trousers.

The invention comprises generally the provision to the wearer of a urinary leg bag a pair of trousers which has a flexible, intermeshing closure on the lower portion of the leg along the inside surface. The closure is sufficiently long so as to permit ready access by the user so that he can quickly discharge the contents of the bag in a short time-period into a toilet or like receptacle.

Accordingly, it is one object of the present invention to provide the wearer of a urinary leg bag with an easy method and device for emptying the bag in a convenient, non-embarrassing manner.

Another object of the present invention is to provide the wearer of a urinary leg bag with a catheter and trouser combination which can be comfortably worn in public without causing embarrassment.

Other objects and advantages of this invention will be apparent from the description and claims which follow, taken together with the appended drawings.

DETAILED DESCRIPTION OF THE PREFERRED EMBODIMENT

Figure 1:
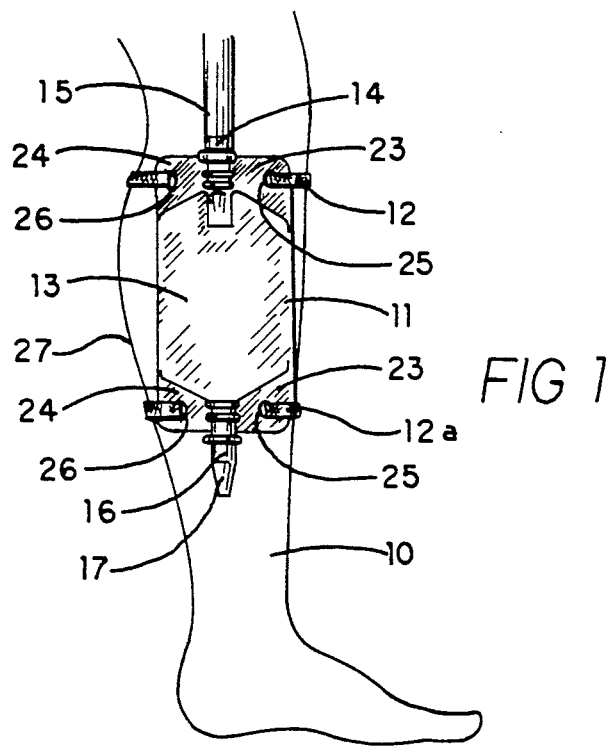
FIG. 1 shows a side view of a disposable urinary leg bag attached to the inside surface of the left leg of a wearer.
Figure 3:
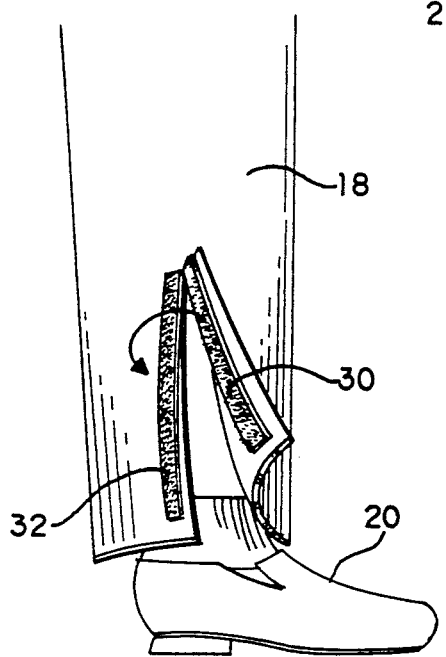
FIG. 3 is a view similar to FIG. 2 showing the left pants leg having a flexible intermeshing closure formed of hook-and-loop fasteners.

Referring now to the drawings, in FIG. 1 the urinary leg bag 13 is attached by latex straps 12 and 12a to the calf region 11 of the inside of the left leg 10 of the wearer so that the entire bag 13 faces the other leg. The elastic latex straps 12 and 12a are attached to tabs 23 and 24 through holes 25 and 26. Connection of straps 12 and 12a to tabs 23 and 24 prevents interference with the bag 13 by straps 12 and 12a.

The lower strap 12a goes under the protrusion of calf 27. The upper strap 12 goes above the protrusion of calf 27. This allows the body's anatomy to hold the bag 13 in place without having straps 12 and 12a pulled very tight, thereby allowing circulation. The bag 13 has an upper connection 14 to the drain 15 from the catheter (not illustrated) that enters the urinary tract. It also has a valve 16 controlling the flow of urine through outlet 17.

Figure 2:
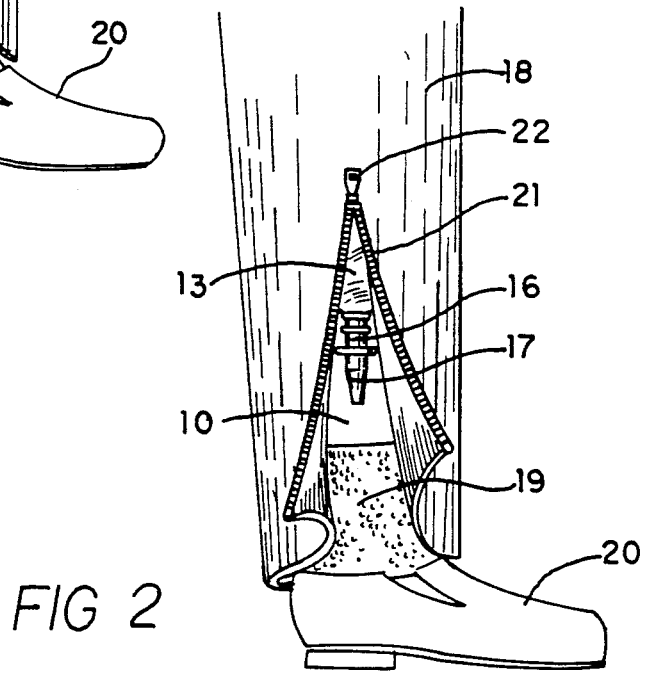
FIG. 2 is a similar view as in FIG. 1, showing the left pants leg covering the bag. The flexible intermeshing closure is shown open to expose the urinary leg bag.

The wearer's trousers 18 have on the inside surface of the left leg 10, extending somewhat from the calf 27 to the ankle, a flexible intermeshing closure 21 which covers the sock 19 and the shoe 20 of the wearer's foot when closed. Some suitable devices for this closure 21 would be hook 30 and loop 32 fastening devices such as VELCRO. Other suitable fasteners could be used. The illustration in FIG. 2 shows a zipper 22.

In operation, the wearer steps up to the toilet bowl so that the outlet 17 is over the bowl and simply zips up or separates the closure 21, thus exposing the valve 16 for opening, so that urine can drain through outlet 17. After the bag 13 is empty the valve 16 is closed and the closure 21 is sealed.

It is to be understood that the present invention is not limited to the sole embodiment described above, but encompasses any and all embodiments within the scope of the following claims.

I claim:

1. A method for draining into a receptacle, employing a urinary drainage leg bag attached to the inside of a calf of a leg of a wearer comprising the steps of:

providing a urinary drainage leg bag having two upper corners and two lower corners and a connection for an incoming catheter drain, an outlet for effecting urine drainage from said urinary drainage leg bag, a valve to open and close said outlet, tabs attached to each corner of said urinary drainage leg bag, said tabls having one hole each, two elastic strap means attached to said tabs through said holes for holding said urinary drainage leg bag onto an inside calf of a leg of a wearer with one of said strap means being above a protrusion of the calf but below the knee of the wearer's leg, and the other of said strap means being below the protrusion of the calf of the wearer's leg, said one of said strap means connecting the hole in one upper corner to the hole in the other upper corner and including means for encircling the leg without traversing the urinary drainage bag, and said other of said strap means connecting the hole in one lower corner to the hole in the other lower corner and including means for encircling the leg without traversing the urinary drainage bag;

providing trousers having on the inside surface of only one trouser leg corresponding to the wearer's leg which will support said urinary drainage leg bag a flexible intermeshing closure extending from the bottom of said trouser leg only up to the location of the trouser leg adapted to overlie the calf protrusion;

placing said urinary drainage leg bag on the wearer so that the bag is supported on the inside of a calf of the wearer with one strap means disposed below the knee and above the calf protrusion and the other strap means disposed below the calf protrusion;

dressing said wearer in said trousers so that the flexible intermeshing closure covers said urinary drainage leg bag when sealed, but allows access to said urinary drainage leg bag when unsealed;

said wearer stepping up to said receptacle;

undoing said trouser flexible intermeshing closure;

placing said outlet over said receptacle;

opening said valve to allow urine to drain out of said urinary drainage leg bag;

closing said valve when said urinary drainage leg bag is empty; and resealing said trouser flexible intermeshing closure over said urinary drainage leg bag; whereby the wearer of the urinary drainage leg bag can unobtrusively empty the leg bag while sitting down or standing up, alone or with assistance.

2. The drainage method according to claim 1, wherein said step of providing trousers includes providing said flexible intermeshing closure in the form of separable interlocking fasteners.

3. The drainage method according to claim 1, wherein said step of providing trousers includes providing said flexible intermeshing closure in the form hook and loop fasteners.

4. In combination:

a urinary drainage leg bag having two upper corners and two lower corners and a connection for an incoming catheter drain, an outlet for effecting urine drainage from said urinary drainage leg bag, a valve to open and close said outlet, tabs attached to each corner of said urinary drainage leg bag, said tabs having one hole each, two elastic strap means attached to said tabs through said holes for holding said urinary drainage leg bag onto an inside of a calf of a leg of a wearer, with one of said strap means being above a protrusion of the calf but below the knee of the wearer's leg, and the other of said strap means being below the protrusion of the calf of the wearer's leg, said one of said strap means connects the hole in one upper corner to the hole in the other upper corner and includes means for encircling the leg without traversing the urinary drainage leg bag, and said other of said strap means connects the hole in one lower corner to the hole in the other lower corner and includes means for encircling the leg without traversing the urinary drainage leg bag; and trousers having on the inside surface of only one trouser leg corresponding to the wearer's leg which will support said urinary drainage leg bag a flexible intermeshing closure extending from the bottom of said trouser leg only up to the location on the trouser leg adapted to overlie the calf protrusion, said flexible intermeshing closure covering said urinary drainage leg bag when sealed, but allowing access to said urinary drainage leg bag when unsealed.

5. The apparatus of claim 4, wherein said flexible intermeshing closure is made up of a plurality of separable interlocking fasteners.

6. The apparatus of claim 4, wherein said flexible intermeshing closure is made of hook and loop fasteners.

* * * * *